US00PP29318P2

(12) United States Plant Patent
Gerdts et al.

(10) Patent No.: US PP29,318 P2
(45) Date of Patent: May 29, 2018

(54) NECTARINE TREE NAMED 'BURNECTTHIRTYTWO'

(50) Latin Name: *Prunus persica nucipersica*
Varietal Denomination: Burnectthirtytwo

(71) Applicants: Timothy J. Gerdts, Kingsburg, CA (US); John K. Slaughter, Fresno, CA (US)

(72) Inventors: Timothy J. Gerdts, Kingsburg, CA (US); John K. Slaughter, Fresno, CA (US)

(73) Assignee: The Burchell Nursery, Inc, Oakdale, CA (US)

( * ) Notice: Subject to any disclaimer, the term of this patent is extended or adjusted under 35 U.S.C. 154(b) by 2 days.

(21) Appl. No.: 15/530,311

(22) Filed: Dec. 21, 2016

(51) Int. Cl.
*A01H 5/08* (2018.01)

(52) U.S. Cl.
USPC ..... Plt./190

(58) Field of Classification Search
USPC ..... Plt./156, 180, 187, 190
See application file for complete search history.

*Primary Examiner* — Susan McCormick Ewoldt
*Assistant Examiner* — Karen M Redden
(74) *Attorney, Agent, or Firm* — Randall Danskin P.S.

(57) ABSTRACT

A new and distinct variety of nectarine tree (*Prunus persica nucipersica*), which is denominated varietally as 'Burnectthirtytwo', and which produces an attractively colored yellow fleshed, clingstone nectarines which is mature for harvesting and shipment approximately July 12 to July 19 under the ecological conditions prevailing in the San Joaquin Valley of central California.

1 Drawing Sheet

Botanical designation: *Prunus persica nucipersica.*
Varietal denomination: Burnectthirtytwo.

BACKGROUND OF THE NEW VARIETY

The present variety of nectarine tree resulted from an on-going program of fruit and nut tree breeding. The purpose of this program is to improve the commercial quality of deciduous fruit and nut varieties, and rootstocks, by creating and releasing promising selections of *Prunus, Malus, Punica* and *Juglans* species. To this end we make both controlled and hybrid cross pollinations each year in order to produce seedling populations from which improved progenies are evaluated and selected.

The seedling, 'Burnectthirtytwo' was originated by us, and selected from a population of seedlings growing in our experimental orchards which are located near Fowler, Calif. The seedlings, grown on their own roots, were derived from planting seed secured from an open-pollinated seedling, 'J10.064' which is non-patented, and which further produces a white-fleshed, clingstone nectarine. The resulting fruit was collected from the open-pollinated seedling at a mature stage, and the seeds were extracted in June of 2005. After a period of stratification, the seed was placed in the greenhouse by population, and then field planted for tree establishment, and ultimately to exhibit fruit for further evaluation. One seedling which produced a yellow fleshed nectarine, which is the present variety, exhibited especially desirable characteristics, and was then designated as 'N53.082'. This new seedling was marked for subsequent observation. After the 2008 fruiting season, the new variety of nectarine tree was selected for advanced evaluation and repropagation.

ASEXUAL REPRODUCTION

Asexual reproduction of this new and distinct variety of nectarine tree was accomplished by budding the newly discovered nectarine tree onto 30 trees established on 'Nemaguard' Rootstock (un-patented). This was performed by us in our experimental orchard which is located near Fowler, Calif. Subsequent evaluations of these asexually reproduced trees have shown those asexual reproductions run true to the original tree. All characteristics of the original tree, and its fruit, were established, and appear to be transmitted through these succeeding asexual propagations.

SUMMARY OF VARIETY

'Burnectthirtytwo' is a new, and distinct variety of nectarine tree, which is considered of relatively large size, and which has a vigorous growth characteristic. This new tree is also a regular and productive bearer of relatively large, firm, yellow-fleshed, acidic, clingstone fruit which have a very good flavor, and eating qualities. This new nectarine tree has a medium chilling requirement of approximately 650 hours, and further produces relatively uniformly sized fruit throughout the tree's canopy. In addition to the foregoing, the fruit of the new nectarine also appears to have good handling and shipping qualities. The 'Burnectthirtytwo' Nectarine tree bears fruit which are typically ripe for commercial harvesting and shipment on approximately July 12 to July 19 under the ecological conditions typically prevailing in the San Joaquin Valley of central California. In relative comparison to the 'Summer Bright' nectarine tree (U.S. Pat. No. 7,049), and which is the closest known variety, the current variety of nectarine tree bears a clingstone fruit that is generally 5.0 millimeters larger. Further, the current variety produces fruit which exhibits a more oblate, and less elongated shape than the fruit produced by the 'Summer Bright' nectarine tree. In relative comparison to the unpatented 'J10.064' nectarine tree, the new variety is clearly distinguished by producing fruit having a yellow flesh, whereas the seed parent 'J10,064' produces fruit having a white flesh characteristic.

BRIEF DESCRIPTION OF THE DRAWINGS

The accompanying drawing, which is provided, is a color photograph of two whole mature fruit harvested from a new tree and which is 5 years old, and which are sufficiently matured for harvesting and shipment. The two mature fruit are viewed from above. One of the fruit is shown resting on its apex, and the other piece of fruit is seen resting on its base. It will be seen that one of the fruit has had a sagittal section removed so as to expose the internal color and condition of the flesh. The colors in this photograph is as nearly true as is reasonably possible in a color representation of this type. Due to chemical development, processing and printing, the fruit depicted in this photograph may, or may not, be accurate when compared to the actual specimen. For this reason, future color references should be made to the color plates (Royal Horticultural Society, Fourth Edition, 2001), and the other descriptions which are provided, hereinafter.

NOT A COMMERCIAL WARRANTY

The following detailed description has been prepared to solely comply with the provisions of 35 U.S.C. § 112, and does not constitute a commercial warranty, (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present new variety.

DETAILED DESCRIPTION

Referring more specifically to the pomological details of this new and distinct variety of nectarine tree, the following has been observed during the tenth fruiting season, and under the ecological conditions prevailing at the orchards of the assignee which are located near the town of Fowler, county of Fresno, state of Calif. All major color code designations are by reference to The R.H.S. Colour Chart (Royal Horticultural Society, Fourth Edition, 2001) provided by The Royal Horticultural Society of Great Britain. Common color names are also occasionally used.

Tree:

*Size*.—Generally considered medium to medium-large in its growth pattern as compared to other common commercial nectarine cultivars ripening in the late season of maturity. The tree of the present variety was pruned to a height of approximately 270.0 cm. to about 310.0 cm. at commercial maturity.

*Width*.—Approximately 265.0 cm.

*Vigor*.—Considered moderately vigorous. The present peach tree variety grew from about 175.0 cm. to about 180.0 cm., in height, during the first growing season. The new variety was then pruned to a height of approximately 150.0 cm. during the first dormant season, and primary scaffolds were then selected for the desired tree structure.

*Productivity*.—Productive. Fruit set varies from more than the desired crop load, to levels higher than desired amounts, when the new variety is grown in a suitable horticultural zone, and under appropriate commercial nursery conditions. The fruit set is spaced by thinning to develop the remaining fruit into the desired market-sized fruit. The number of the fruit set varies with the prevailing climatic conditions, and the cultural practices employed.

*Fruit bearing*.—Regular. Fruit set has been more than adequate during the previous years of observation, and thinning was necessary during the past 10 years on both the original seedling, and on subsequent asexually reproduced trees.

*Tree form*.—Upright, and pruned into a vase shape.

*Tree density*.—Considered moderately dense. It has been discovered that pruning the branches from the center of the new tree to obtain a resulting vase shape allows for enhanced air movement, and appropriate amounts of sunlight to enter the tree canopy so as to improve the resulting fruit color, and a renewal of fruiting wood throughout the tree canopy.

*Hardiness*.—The present tree was grown and subsequently evaluated in USDA Hardiness Zone 9. The calculated winter chilling requirements of the new tree is approximately 500 hours at a temperature below 7.0 degrees C. The present variety appears to be hardy under typical central San Joaquin Valley climatic conditions.

Trunk:

*Diameter*.—Approximately 17.5 cm in diameter when measured at a distance of approximately 15.24 cm. above the soil level. This measurement was taken from one of the new trees at the end of the 7th growing season.

*Bark texture*.—Considered moderately rough, and displaying folds of papery scarfskin. Since bark development and coloration change with advancing tree age this characteristic varies with the tree vigor, tree age and the regional environmental conditions under which the tree was grown. Therefore, this is not a dependable descriptor for the new variety.

*Lenticels*.—Numerous flat, and oval lenticels are present. The lenticels range in size from approximately 5.0 millimeters to about 7.0 mm. in width; and between about 1.0 and about 2.0 millimeters in height. The development and size of the trunk lenticels can be influenced, to some degree, by the ambient growing conditions experienced by the tree, and are not, necessarily, a dependable characteristic for this variety. As trees of this new variety mature, lenticels are present, but they are typically covered, over time, by increasing layers of cork (mature bark), and therefore become less apparent to an observer.

*Lenticel color*.—Considered an orange brown, (RHS Greyed-Orange Group 164 B).

*Bark coloration*.—Variable, but it is generally considered to be a greyed brown, (RHS Grey-Green Group 197 B). This bark description was taken from trees that were six years old and which have further ruptured the scarf skin, and which further also have developed bark furrowing that is much more typical of the bark of older trees. It should also be noted that the coloration of the bark is influenced, and varies, as the smoother, darker background color of the bark approaches other bark features such as the lenticels, and the initial fissures form a feature of the scarf skin development.

Branches:

*Size*.—Considered medium large for the variety.

*Branch diameter*.—Average as compared to other nectarine varieties. The branches have an average diameter of about 11.0 centimeters when measured during the 6th year after grafting.

*Flowering shoot thickness*.—Average for the species. Generally, the most consistent flower bud development, and therefore potential fruiting sites occur on shoots which are approximately 5.0 millimeters in diameter, or larger, but generally less than 13.0 millimeters in diameter, at the time of bloom.

*Surface texture*.—Average, and appearing relatively smooth but with more furrowing being observed on wood which is several years old.

*Crotch angles*.—Primary branches are considered variable, and are usually growing at an angle of about 42 to about 50 degrees when measured from a horizontal plane. This particular characteristic can vary due to the influence of the variable ecological conditions, and cultural practices which are employed.

*Current season shoots*.—Surface texture — Substantially glabrous.

*Internode length*.—Approximately 2.4 cm.

*Color of mature branches*.—Generally speaking a grey-brown, (RHS Greyed-Orange Group 177 C).

*Current season's shoots*.—Color. — Light green, (RHS Yellow-Green Group 145 C). The color of the new shoot tips is considered a bright and shiny green (RHS Yellow-Green Group 146 D). The vegetative shoot color can be significantly influenced by plant nutrition, irrigation practices, and exposure to sunlight, and therefore should not be considered a consistent botanical characteristic of this new variety of tree.

Leaves:

*Size*.—Considered somewhat elongated and narrow for the species. Leaf measurements have been taken from vigorous, upright, current-season growth, taken at approximately mid-shoot. It should be understood that the leaf size is often influenced by the prevailing growing conditions, quality of sunlight, and the location of the leaf within the tree canopy. For this reason, leaf sizes can vary somewhat significantly based upon the ambient and other cultural factors listed above, and are not typically considered a dependable botanical descriptor.

*Leaf length*.—Approximately 148.0 to about 155.0 millimeters.

*Leaf width*.—Approximately 30.0 to about 33.0 millimeters.

*Leaf base-shape*.—The leaves generally exhibit substantially equal marginal symmetry relative to the leaf longitudinal axis.

*Leaf form*.—Lanceolate.

*Leaf tip form*.—Acuminate.

*Leaf color*.—Upper Leaf Surface — Medium green, (approximately RHS Green Group 137 A).

*Leaf texture*.—Upper and Lower Leaf Surfaces — Glabrous. Leaf Color. — Lower Leaf Surface — Medium green, (approximately RHS Green Group 146 B).

*Leaf venation*.—Pinnately veined.

*Mid-vein*.—Color — Considered a light yellow, (approximately RHS Greyed-Yellow Group 160 C) in the early to mid-period of the growing season.

*Leaf margins*.—Gently undulating. Marginal Form. — Considered finely crenate. Marginal Uniformity. — Generally uniform.

*Leaf petioles*.—Form. — Considered canaliculated, and having a more pronounced trough when viewed from the dorsal aspect. The petiole margin is considered rounded when viewed from the ventral aspect. Size. — Considered medium-small for the species. Length. — About 8.0 to about 11.0 mm. Diameter. — About 1.5 to about 2.0 mm. Leaf Petiole Color. — Light yellow green, (approximately RHS Yellow-Green Group 145 A). Texture. — Glabrous. Strength. — Generally considered durable for the species until senescence is reached.

*Leaf glands*.—Size. — Considered relatively small for the species; approximately 2.0 mm. in length; and about 1.0 mm. in height. Number. — Generally one, and less commonly two glands appear along each marginal side. Observations of more than two glands per marginal side are very uncommon. Type. — Leaf glands located at the base of the leaf are predominantly reniform in shape. An additional one to two, or occasionally more leaf glands, which appear reniform, and stalked, are often present at the basal margin of the leaf petiole as well. Color. — Considered a medium-dark brown, approximately (RHS Brown Group 199 A). Typically the coloration of the glands darkens, and occasionally begins to desiccate during the mid-late growing season.

*Leaf stipules*.—Size. — Medium large for this variety. Numbers. — Typically 2 per leaf bud, and up to 6 per shoot tip are seen. Form. — Lanceolate in form, and having a serrated marginal edge. Color. — Green, (approximately RHS Green Group 137 B) when young, but graduating to a brown color, (approximately RHS Greyed-Orange Group 165 A) with advancing senescence. The leaf stipules are generally considered to be early deciduous.

Flower buds:

*Hardiness*.—No winter injury (bud death) has been seen during the last several years of observation in the central San Joaquin Valley. The new variety of nectarine tree has not been intentionally subjected to drought, cold or heat stress, and therefore this information is not available.

*Flower bud*.—Size — Variable, and dependent upon the state of maturity. The flower buds as described were observed approximately 7 days prior to bloom, about Feb. 13, 2016. Length — Approximately 15.5 millimeters. Diameter — Approximately 8.5 millimeters. Surface Texture. — Pubescent. Orientation. — Considered appressed, but appearing less so as the blossoms near opening.

*Bud scale color*.—Approximately RHS Greyed-Orange Group 175 A.

Flowers:

*Date of first bloom*.—Observed on Feb. 20, 2016. Blooming Time. — Considered average in relative comparison to other commercial nectarine cultivars grown in the central San Joaquin Valley. The date of full bloom was observed on Feb. 28, 2016. The date of full bloom varies slightly with climatic conditions, and the prevailing cultural practices which are employed.

*Duration of bloom*.—Approximately 8 or more days. This particular characteristic varies slightly with the prevailing climatic conditions.

*Flower class*.—Considered a perfect flower, complete and perigynous.

*Flower type*.—The variety is considered to have a showy-type flower.

*Flower size*.—Considered large. The flower diameter at full bloom is approximately 57.0 to 60.0 millimeters.

*Bloom quantity*.—Considered abundant.

*Flower bud density*.—Generally considered dense.

*Flower bud frequency*.—Generally two flower buds appear per node, and occasionally one flower bud per node is observed. On very rare occasions three floral Bud's per node are observed.

*Petal size*.—Generally considered large for the species. Petal Length. — Approximately 26.0 to 28.0 millimeters. Petal Width. — Approximately 21.0 to 26.0 millimeters.

*Petal form*.—Considered broadly ovate.

*Petal count*.—Nearly always 5.

*Petal texture*.—Upper and Lower Petal Textures. — Very finely pubescent, and satin like.

*Petal color*.—Considered a light pink at the popcorn stage, (RHS Red-Purple Group 65 B); and darkening with advanced senescence, and the exposure of sunlight, to a medium-dark pink, (RHS Red-Purple 63 C). This darkening of the petal color is generally most noticeable within the margins of the petal claw.

*Fragrance*.—Slight.

*Petal claw*.—Form. — The claw is considered ovate, and is generally large in size. Length. — Approximately 14.0 to 16.0 millimeters. Width. — Approximately 10.5 to 14.0 millimeters.

*Petal margins*.—Generally speaking, they are moderately undulate and ruffled, especially apically.

*Petal apex*.—Generally — The petal margin often exhibits a shallow, and wide recess at the tip. Width — Approximately 2.5 to 4.0 millimeters. Depth. — 1.0 to 2.0 millimeters.

*Flower pedicel*.—Length. — Considered medium-long with an approximate length of about 1.5 to about 3.5 millimeters. Diameter. — Approximately 2.5 millimeters. Flower Pedicel Color. — A medium brown, approximately (RHS Grey-Brown Group N199 D) depending upon the pedicel, and fruit maturity, and the timing of the visual observation. Strength. — Tenacious. This is considered average for the species. Texture. — Generally smooth, to slightly undulate.

*Floral nectaries*.—Color. — Considered a dull brown (approximately RHS Greyed-Orange Group 175 B).

*Calyx*.—Surface Texture. — Generally glabrous. Color. — A dull grey purple, (approximately RHS Greyed-Purple Group 185 B).

*Sepals*.—Upper Surface Texture. — Moderately pubescent. Lower Surface Texture. — Finely pubescent. Number. — 5 sepals are usually observed. Size. — Generally medium large. Sepal Length. — Approximately 5.0 to 8.0 millimeters. Sepal Width. — Approximately 4.0 to 6.0 millimeters. Sepal Shape. — Generally obovate. Sepal Margin. — Considered smooth, and entire. Sepal Color. — A dull grey purple, (approximately RHS Greyed-Green Group 197 B).

*Anthers*.—Size. — Average. Color. — Yellow when viewed dorsally, and prior to dehiscence, (approximately RHS Greyed-Yellow Group 162 B). Position Relative to the Stigma. — Generally the stigma is superior to the anthers by approx. 1.0-2.0 millimeters.

*Pollen production*.—Pollen is abundant, and has a yellow color, (approximately RHS Yellow-Orange Group 18 A).

*Fertility*.—Self-fertile.

*Filaments*.—Size. — Approximately 17.5 to 20.0 millimeters in length. Color. — Generally considered white, (RHS Red Yellow Group 11 D).

*Pistil*.—Number. — Usually one, and only rarely more than one is observed. Size. — Generally considered large. Length. — Approximately 19.0 to about 22.0 millimeters, including the ovary. Color. — Considered a very pale green, (approximately RHS Yellow-Green Group 154 D). Surface Texture. — The variety has a long glabrous pistil. Position Relative to the Petals. — At flower maturity the stamens grow to be superior to the petals.

Fruit:

*Maturity when described*.—Firm ripe condition (shipping ripe).

*Date of first picking*.—Approximately Jul. 8, 2016.

*Date of last picking*.—Jul. 14, 2016. The date of harvest can vary with the prevailing climatic conditions, crop loads and the cultural practices which are employed.

*Size*.—Generally — Considered medium-large.

*Average cheek diameter*.—Approximately 76.0 to about 80.0 millimeters.

*Average axial diameter*.—Approximately 74.0 to about 79.0 millimeters.

*Typical weight*.—Approximately 225.0 grams. This characteristic is quite dependent upon the prevailing cultural practices, and ambient growing conditions. Consequently this characteristic is not particularly distinctive of the new variety.

*Fruit form*.—Generally — Considered globose. The fruit is generally very uniform in its symmetry.

*Mucron tip*.—Absent.

*Fruit suture*.—No stitching exists along the suture line.

*Suture*.—Color — Generally, the fruit suture appears blushed to the same degree as the skin, (approximately RHS Orange-Red Group 34 A).

*Ventral surface*.—Form — Considered even, and uniform in appearance, when it is viewed from the lateral, sutural plane.

*Apex*.—Shape — Rounded to slightly rutuse.

*Base*.—Shape — Generally smooth.

*Stem cavity*.—Generally — The stem cavity has a rounded circular form or shape which is usually considered uniform. The rounded stem cavity slightly extends toward the suture. The average depth of the stem cavity is about 8.0-10.0 mm. The average width of the stem cavity is about 26.0 mm. The average length of the stem cavity, when measured in the suturial plane, is about 45.0 mm.

*Fruit skin*.—Thickness. — Considered medium in thickness, and tenacious to the flesh. Surface Texture. — Glabrous. Taste. — Non-astringent. Tendency to crack. — Not observed in the previous years of observation and evaluation.

*Fruit skin color*.—Blush Color. — Generally speaking, a red blush exists on a majority of the skin of the fruit (approximately RHS Orange-Red Group 34 A), and is more typically present on the portions of the fruit facing the sunlight. The blush of the fruit typically covers approximately 75%-95% of the fruit skin surface. The percentage of the blush on the fruit skin surface can vary, and is generally dependent upon the fruit's exposure to direct sunlight; specific fruit maturity; and also the prevailing ecological and cultural conditions under which the fruit was grown.

*Ground color*.—A medium, light orange yellow, (approximately RHS. Yellow-Orange Group 23 C). The ground color of the fruit can vary significantly based upon the maturity of the fruit when this measurement is taken, and generally acquires a lighter, and less green cast with increasing maturity.

*Fruit glossiness*.—The fruit is considered to be glossy.

*Fruit stem*.—Size. — Medium in length, approximately 6.0 to about 8.0 millimeters. Diameter. — Approximately 2.0 to about 3.0 millimeters. Color. — Pale yellow-green, (approximately RHS Yellow-Green Group N144 C).

*Fruit flesh*.—Ripening. — Considered even. Texture. — Considered firm, crunchy, juicy and dense. Fibers. — Present, but not prominent. Aroma. — Slight. Eating Quality. — Considered very good. Flavor. — Considered balanced with both sweetness, and acidity. Juice Production. — Moderate. Brix. — About 11.0 to 13.5 degrees. This particular characteristic varies slightly with the number of fruit per tree; the maturity of the fruit when harvested; the prevailing cultural practices employed in growing the new tree; and the ambient climatic conditions. Acidity. — Considered low. Approximately 0.8 titratable acidity is typically detected. The acid levels assayed from fruit flesh can vary based upon the fruit maturity, sunlight exposure, and the climatic, regional and cultural influences the tree was exposed to. Flesh Color. — It is considered yellow, (approximately RHS Yellow-Orange Group 17 D). A slight pigmentation of pink red can be seen radiating from the stone (approximately RHS Red Group 39 A).

Stone:

*Stone type*.—Considered a clingstone.

*Stone size*.—It is generally considered to be medium for the species. The stone size varies significantly depending upon the tree vigor, the crop load, and the prevailing growing and cultural conditions under which the tree was grown.

*Stone length*.—Average, about 30.0 to about 35.0 millimeters.

*Stone width*.—Average, about 23.0 to about 27.0 millimeters.

*Stone diameter*.—Average, about 17.0 to about 20.0 millimeters.

*Stone form*.—Roughly ovoid.

*Stone base*.—Shape — The stone is considered shortly attenuate.

*Stone apex*.—Shape — The stone exhibits a slightly acute apex.

*Stone surface texture*.—Considered irregularly furrowed toward the apex. Further, more pitting exists in the mid-portion of the stone (laterally), and is more commonly observed toward the base. Stone Ridges. — Ridging is generally more prominent, and is usually oriented parallel, and laterally relative at the ventral and dorsal margins. Stone Ventral Edge. — The ventral edge has adjoining ridges formed from each hemisphere. There are longitudinal grooves running alongside this joined, ventral suture. Secondarily, there can exist an additional set of parallel ridges, one on each side of the major ridge. These secondary ridges are less prominent, and do not always extend from the hilum to the apex. Dorsal Edge. — Shape — Generally considered even. The folds of the surface ridges appearing on the external margins often end gently along the suture.

*Stone color*.—The color of a mature, dry stone is generally considered a dull brown, approximately (RHS Greyed-Orange Group 165 D). The stone color can vary considerably based upon how recently the fruit has ripened; the degree of oxidation it has experienced; and any blanching which has taken place by way of exposure of the stone to sunlight.

*Tendency to split*.—Splitting has rarely been noted.

*Kernel*.—Length. — Approximately 16.0-19.0 millimeters. Width. — Approximately 12.0-15.0 millimeters. Thickness. — 4.0-6.0 millimeters. Size. — The kernel is considered medium in size. Form. — Considered generally ovoid. Kernel Surface Texture. — The kernel pellicle is shortly pubescent. Color. — A dark tan (RHS Greyed-Orange Group 165 C).

*Use*.—The present variety 'Burnectthirtytwo' is considered to be a nectarine tree of the late season of maturity, and which produces fruit which are considered to be firm, attractively colored, and which further are useful for both local and long distance shipping.

*Keeping quality*.—Appears excellent. The fruit of the present variety has stored well for periods of up to 35 days after harvest at 1.0 degree Celsius.

*Shipping quality*.—Good. The fruit of the new nectarine tree variety showed minimal bruising of the flesh or skin damage after being subjected to normal harvesting and packing procedures.

*Resistance to insects and disease*.—No particular susceptibilities were noted. The present variety of nectarine tree has not been intentionally tested to expose or detect any susceptibilities or resistances to any known plant, fruit diseases, insect, frost, winter injury or other environmental factors. Although the new variety of nectarine tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management practices are to be expected.

Having thus described and illustrated our new variety of nectarine tree, what we claim is new, and desire to secure by plant Letters Patent is:

1. A new distinct variety of nectarine tree, substantially as illustrated and described, and which is characterized principally as to novelty by producing an attractively colored yellow fleshed, clingstone nectarine which is mature for harvesting and shipment approximately July 12 to July 19 under the ecological conditions prevailing in the San Joaquin Valley of central California.

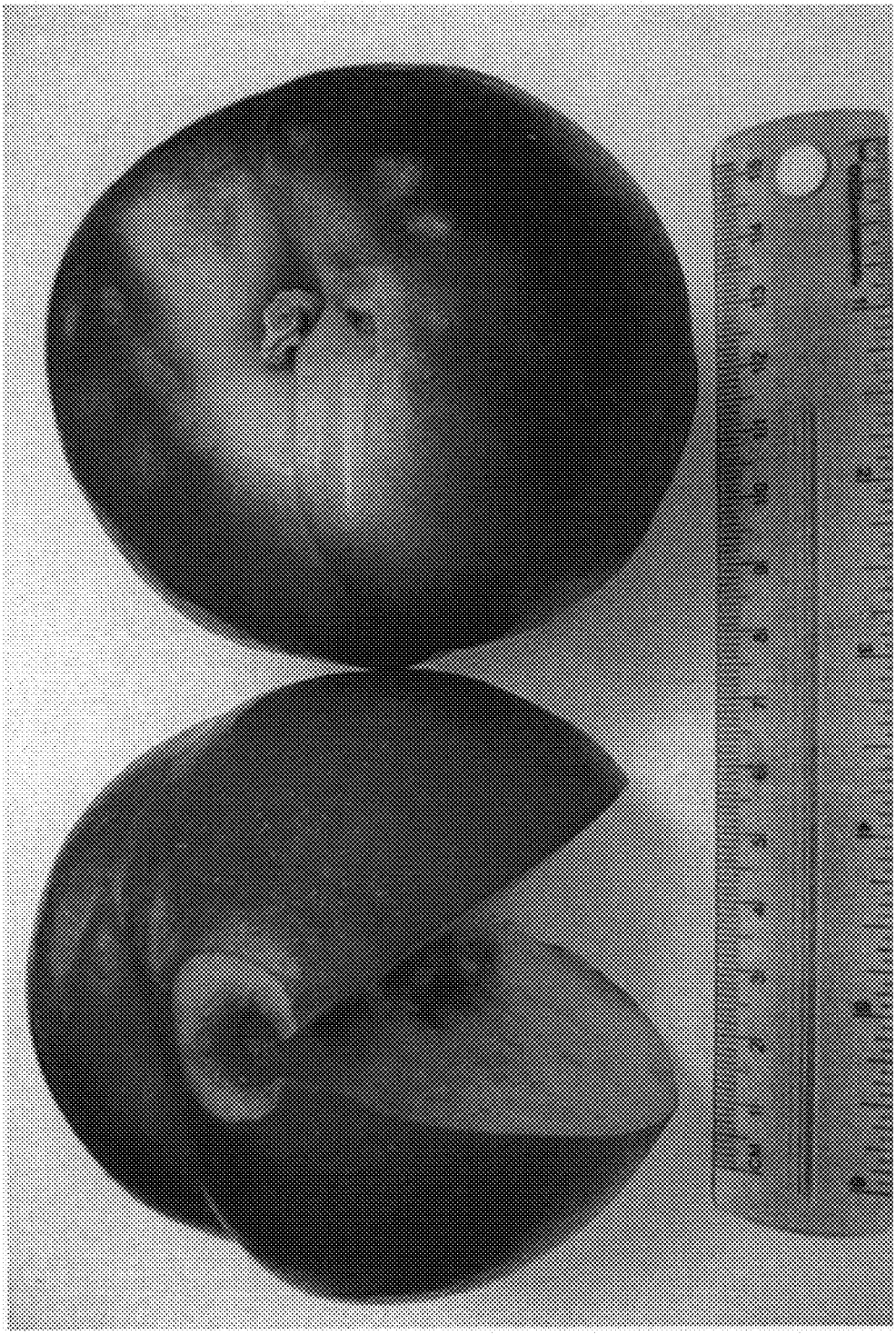

* * * * *